United States Patent
Plambech et al.

(10) Patent No.: US 9,750,886 B2
(45) Date of Patent: Sep. 5, 2017

(54) DRUG DELIVERY DEVICE WITH DOSE CAPTURING MODULE

(71) Applicant: Novo Nordisk A/S, Bagsvaerd (DK)

(72) Inventors: Christian Plambech, Soeborg (DK); John Oestergaard Madsen, Roedovre (DK); Jesper Peter Windum, Hilleroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 24 days.

(21) Appl. No.: 14/767,315

(22) PCT Filed: Feb. 19, 2014

(86) PCT No.: PCT/EP2014/053221
§ 371 (c)(1),
(2) Date: Aug. 12, 2015

(87) PCT Pub. No.: WO2014/128157
PCT Pub. Date: Aug. 28, 2014

(65) Prior Publication Data
US 2015/0367077 A1    Dec. 24, 2015

Related U.S. Application Data

(60) Provisional application No. 61/767,815, filed on Feb. 22, 2013.

(30) Foreign Application Priority Data

Feb. 19, 2013    (EP) ..................................... 13155799

(51) Int. Cl.
*A61M 5/315*    (2006.01)
*A61M 5/145*    (2006.01)
*A61M 5/50*    (2006.01)

(52) U.S. Cl.
CPC ...... *A61M 5/31528* (2013.01); *A61M 5/1452* (2013.01); *A61M 5/31533* (2013.01);
(Continued)

(58) Field of Classification Search
CPC .......... A61M 5/31528; A61M 5/31533; A61M 5/31541; A61M 5/31546; A61M 5/31551
(Continued)

(56) References Cited

U.S. PATENT DOCUMENTS 4,807,248 A    2/1989    Pyatt et al.
4,854,324 A    8/1989    Hirschman et al.
(Continued)

FOREIGN PATENT DOCUMENTS

EP    1198811 A1    4/2002
EP    2060284 A1    5/2009
(Continued)

*Primary Examiner* — Kevin C Sirmons
*Assistant Examiner* — Deanna K Hall
(74) *Attorney, Agent, or Firm* — Wesley Nicolas

(57) ABSTRACT

A drug delivery system is provided including a drug expelling structure adapted to expel a set dose from a drug-filled cartridge, the expelling structure including a rotational member adapted to rotate relative to a housing and corresponding to a set and/or expelled dose, the system including a sensor adapted to detect a set and/or an expelled dose. The sensor includes a first portion mounted to and rotating with the rotational member, and a second portion including a second rotary sensor part mounted non-rotationally relative to the housing. The first portion includes electronic circuitry, and a first rotary sensor part, and the second portion includes a second rotary sensor part mounted non-rotationally relative to the housing. The first and second rotary sensor parts rotate relative to each other during setting and/or expelling of a dose of drug.

15 Claims, 8 Drawing Sheets

(52) U.S. Cl.
CPC ....... *A61M 5/5086* (2013.01); *A61M 2205/33* (2013.01); *A61M 2205/52* (2013.01)

(58) Field of Classification Search
USPC ........................................................ 604/211
See application file for complete search history.

(56) References Cited

U.S. PATENT DOCUMENTS

| | | |
|---|---|---|
| 4,891,476 A | 1/1990 | Nation et al. |
| 5,315,077 A | 5/1994 | Simon et al. |
| 5,669,489 A | 9/1997 | von Ende |
| 5,739,775 A | 4/1998 | Brandestini |
| 5,847,335 A | 12/1998 | Sugahara et al. |
| 5,951,398 A | 9/1999 | Yamamoto et al. |
| 7,008,399 B2 | 3/2006 | Larsen et al. |
| 7,138,806 B2 | 11/2006 | Gafner et al. |
| 7,635,817 B2 | 12/2009 | Asada |
| 8,221,356 B2 | 7/2012 | Enggaard et al. |
| 2005/0115317 A1 | 6/2005 | Fouquet |
| 2006/0224123 A1 | 10/2006 | Friedli et al. |
| 2008/0033369 A1 | 2/2008 | Kohlbrenner et al. |
| 2008/0135090 A1 | 6/2008 | Corrales |
| 2009/0318865 A1* | 12/2009 | Moller .............. A61M 5/31553 604/135 |
| 2010/0145656 A1 | 6/2010 | Koehler et al. |
| 2011/0313349 A1 | 12/2011 | Krulevitch et al. |
| 2011/0313395 A1 | 12/2011 | Krulevitch et al. |
| 2012/0041363 A1 | 2/2012 | ielDan |
| 2012/0043131 A1 | 2/2012 | Christov et al. |
| 2013/0176020 A1 | 7/2013 | Chauvin et al. |
| 2016/0008552 A1 | 1/2016 | Madsen et al. |
| 2016/0015903 A1 | 1/2016 | Madsen et al. |
| 2016/0175527 A1 | 6/2016 | McCullough |
| 2016/0287804 A1 | 10/2016 | Madsen et al. |
| 2016/0287807 A1 | 10/2016 | Madsen et al. |
| 2016/0287808 A1 | 10/2016 | Madsen |

FOREIGN PATENT DOCUMENTS

| | | |
|---|---|---|
| EP | 1881859 B1 | 1/2011 |
| GB | 2456367 A | 7/2009 |
| WO | 96/19872 A1 | 6/1996 |
| WO | 9619872 A1 | 6/1996 |
| WO | 2005004955 A1 | 1/2005 |
| WO | 2006045525 A1 | 5/2006 |
| WO | 2008037801 A1 | 4/2008 |
| WO | 2008091838 A2 | 7/2008 |
| WO | 2008146282 A2 | 12/2008 |
| WO | 2009024562 A1 | 2/2009 |
| WO | 2010052275 A2 | 5/2010 |
| WO | 2010098927 A1 | 9/2010 |
| WO | 2010128493 A2 | 11/2010 |
| WO | 2011038703 A1 | 4/2011 |
| WO | 2011064299 A1 | 6/2011 |
| WO | 2012140097 A2 | 10/2012 |
| WO | 2013010889 A1 | 1/2013 |
| WO | 2013/083715 A1 | 6/2013 |
| WO | 2013/098421 A1 | 7/2013 |
| WO | 2014/128156 A1 | 8/2014 |
| WO | 2014/128157 A1 | 8/2014 |

* cited by examiner

DRUG DELIVERY DEVICE WITH DOSE CAPTURING MODULE

CROSS-REFERENCE TO RELATED APPLICATIONS

This application is a 35 U.S.C. §371 National Stage application of International Application PCT/EP2014/053221 (published as WO 2014/128157), filed Feb. 19, 2014, which claims priority to European Patent Application 13155799.3, filed Feb. 19, 2013; this application claims priority under 35 U.S.C. §119 to U.S. Provisional Application 61/767,815; filed Feb. 22, 2013.

The present invention relates to a device and a system for capturing drug delivery dose data. Especially, the invention addresses the issue of providing an electronic data capturing module in and for a drug delivery device and system.

BACKGROUND OF THE INVENTION

In the disclosure of the present invention reference is mostly made to the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Correspondingly, a number of injection devices with a dose monitoring/acquisition feature has been provided, see e.g. in US 2009/0318865, WO 2010/052275 and U.S. Pat. No. 7,008,399. However, most devices of today are without it.

Having regard to the above, it is an object of the present invention to provide a drug delivery device and system as well as components therefore which cost-effectively and reliably allows detection and storage of dose data related to use of a drug delivery device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a drug delivery device is provided, comprising a housing, a drug-filled cartridge or means for receiving a drug-filled cartridge, the cartridge comprising an axially displaceable piston and a distal outlet portion, and drug expelling means. The drug expelling means comprises dose setting means allowing a user to set a dose of drug to be expelled, an axially displaceable piston rod adapted to move the piston of a cartridge in a distal direction to thereby expel drug from the cartridge, and a rotational member adapted to rotate relative to the housing and corresponding to a set and/or expelled dose. The drug delivery device further comprises sensor means adapted to detect a set and/or an expelled dose, the sensor means comprising first and second portions. The first portion is mounted to and rotates with the rotational member, the first portion comprising electronic processor circuitry, and a first rotary sensor part. The second portion comprises a second rotary sensor part mounted non-rotationally relative to the housing, whereby the first and second rotary sensor parts rotate relative to each other during setting and/or expelling of a dose of drug.

Such an arrangement allows a rotary sensor assembly to be incorporated cost-effectively and reliably in a drug delivery device comprising a rotational member which rotates corresponding to a set and/or expelled dose. As the first portion comprises the electronic processor circuitry it could also be considered the main portion of the sensor means. By integrating electronic processor circuitry with the rotating sensor part a simpler design which can be manufactured and assembled more cost-effectively is provided. The processor circuitry will typically comprise a processor in the form of a microprocessor, microcontroller or CPU which may be of a general purpose design or be specifically designed for the actual device.

In an exemplary embodiment the rotational member is rotated from an initial position to a set position when a dose is set, and the rotational member is rotated from the set position to the initial position when the set dose is expelled. Alternatively, the rotational member is in the form of a setting member which is rotated to set a dose, however, the setting member is moved axially during expelling. In a further alternative, a rotational member is moved axially (or not moved) during setting of a dose, the member being rotated during expelling of a dose.

The rotational member may be adapted to move axially between an initial and an actuated position, the main portion being mounted to move axially with the rotational member. Also the second portion may be mounted to move axially with the rotational member. By adapting the main (and second) sensor portion to move axially with the rotational member a further degree of freedom for integrating the sensor means in a given expelling assembly design is provided. Further, the sensor means may be adapted to detect when the rotational member is moved axially between the initial and the actuated position, this allowing the sensor means to detect different operational states of a given expelling mechanism.

The electronic processor circuitry may comprise logging means adapted to create a log for dose amounts of drug expelled from a cartridge by the drug expelling means. The dose amounts are calculated based on relative rotation between the first and second rotary sensor parts. The dose amounts may be determined "directly" by sensing relative rotation during expelling of a dose of drug, or they may be estimated "indirectly" by sensing relative rotation during setting of a dose of drug to be expelled, i.e. it is assumed that the set dose is expelted.

The main portion may be provided with a display which may be controlled such that it is turned off during rotation, this preventing that a user is distracted by a rotating display. In this way the interior design of the drug delivery device is kept hidden for the eyes of the user. Further or alternatively, the electronic processor circuitry may comprise transmitter means adapted to transmit stored data to an external receiver, e.g. by means of NFC.

The sensor means may be provided in the form of an electronic assembly comprising the first and the second portion, the first portion being in the form of an electronic module, the second portion being rotationally mounted on the electronic module. In such a design the electronic module and the rotational member comprises corresponding interconnecting means allowing the electronic module to be mounted rotationally locked to the rotational member, and the second portion and the housing comprises corresponding interconnecting means allowing the second rotary sensor part to be mounted rotationally locked relative to the housing. Such a design allows a sensor module to be manufactured and mounted in a cost-effective way.

In an exemplary embodiment the first rotary sensor part comprises a pattern of a plurality of individual electrically conducting sensor areas connected to the electronic processor circuitry, and the second rotary sensor part comprises at least one contact structure adapted to engage and connect different sensor areas as the first and second part of the rotary sensor rotate relative to each, the connections being indicative of a rotational position or movement between the first and second portions. To further enhance the functionality one of the contact structures may comprise an axial switch contact having a connected position in which the switch contact is in contact with a sensor area and a dis-connected position in which the switch contact is not in contact with a sensor area, wherein the axial switch contact is adapted to be moved between the connected position and the dis-connected position when the second rotary sensor part is moved axially relative to the housing. In an exemplary embodiment the second rotary sensor part is in the form of a metallic disc member comprising a plurality of integrally formed flexible arms forming the contact structures, at least one of the flexible arms being axially moveable to form a flexible switch arm comprising the axial switch contact.

Instead of the above-described contact-based rotary sensor design alternative means for detecting relative rotation between the two parts may be used. For example, detection could be based on magnetic or optical contact-less technology.

As indicated above, the sensor means may be provided as an electronic assembly allowing for cost-effective manufacture and mounting. Correspondingly, in a further aspect of the invention a drug delivery system is provided comprising a drug delivery assembly as well as first and second modules. The drug delivery device comprises a housing, a drug-filled cartridge or means for receiving a drug-filled cartridge, as well as drug expelling means, the cartridge comprising an axially displaceable piston and a distal outlet portion. The drug expelling means comprises dose setting means allowing a user to set a dose of drug to be expelled, an axially displaceable piston rod adapted to move the piston of a cartridge in a distal direction to thereby expel drug from the cartridge, a rotational member adapted to rotate corresponding to a set and/or expelled dose, and an axially moveable release member adapted to release the drug expelling means to thereby expel the set dose of drug. The first and second modules each comprises first coupling means allowing the module to be mounted non-rotationally to the rotational member, wherein a mounted module serves to transfer an axially directed force acting to move the release member. The first module comprises no electronic processor circuitry, whereas the second module is a self-contained sensor module, comprising (i) a first portion having the first coupling means, electronic processor circuitry, and a first rotary sensor part, and (ii) a second portion having a second rotary sensor part mounted rotationally relative to the housing, and second coupling means allowing the second rotary sensor part to be mounted non-rotationally to the housing, whereby the first and second rotary sensor parts of a mounted sensor module rotate relative to each other during setting and/or expelling of a dose of drug to thereby detect a set and/or expelled dose. By such a system design drug delivery devices with and without dose sensing means can be provided in a modular and cost-effective way.

The drug delivery system may comprise a rotatable dose setting member, the rotational member being adapted to rotate corresponding to a set dose, wherein a mounted module serves to transfer a rotational movement of the dose setting member to the rotatable member. By this design each of the modules serves to mechanically transfer both axial and rotational movement.

As used herein, the term "drug" is meant to encompass any flowable medicine formulation capable of being passed through a delivery means such as a cannula or hollow needle in a controlled manner, such as a liquid, solution, gel or fine suspension, and containing one or more drug agents. The drug may be a single drug compound or a premixed or co-formulated multiple drug compounds drug agent from a single reservoir. Representative drugs include pharmaceuticals such as peptides (e.g. insulins, insulin containing drugs, GLP-1 containing drugs as well as derivatives thereof), proteins, and hormones, biologically derived or active agents, hormonal and gene based agents, nutritional formulas and other substances in both solid (dispensed) or liquid form. In the description of the exemplary embodiments reference will be made to the use of insulin and GLP-1 containing drugs, this including analogues thereof as well as combinations with one or more other drugs.

BRIEF DESCRIPTION OF THE DRAWINGS

In the following the invention will be further described with reference to the drawings, wherein.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The terms "assembly" and "subassembly" do not imply that the described components necessarily can be assembled to provide a unitary or functional assembly or subassembly during a given assembly procedure but is merely used to describe components grouped together as being functionally more closely related.

Figure 1:
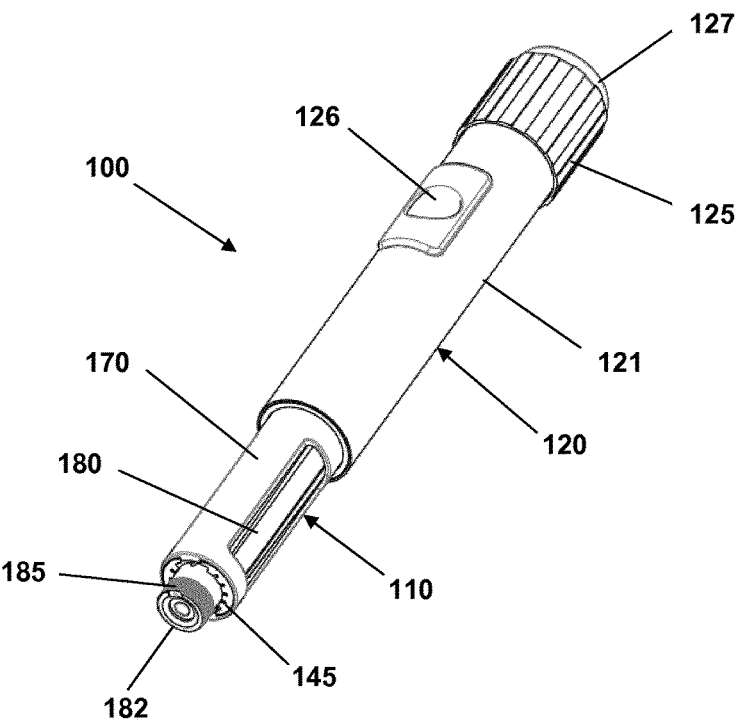
FIGS. 1 and 2 show a front-loaded drug delivery device with respectively without a drug cartridge mounted.

Referring to FIG. 1 a pen-formed drug delivery device 100 will be described. The device represents a "generic" drug delivery device providing an example of a device in combination with which embodiments of the present invention is intended to be used, such a device comprising a rotational member adapted to rotate corresponding to a set and/or expelled dose of drug.

More specifically, the pen device comprises a cap part (not shown) and a main part having a proximal body or drive assembly portion 120 with a housing 121 in which a drug expelling mechanism is arranged or integrated, and a distal cartridge holder portion in which a drug-filled transparent cartridge 180 with a distal needle-penetrable septum can be arranged and retained in place by a cartridge holder 110 attached to the proximal portion, the cartridge holder having openings allowing a portion of the cartridge to be inspected. The cartridge may for example contain an insulin, GLP-1 or growth hormone formulation. The device is designed to be loaded by the user with a new cartridge through a distal receiving opening in the cartridge holder, the cartridge being provided with a piston driven by a piston rod 128 forming part of the expelling mechanism. A proximal-most rotatable dose ring member 125 serves to manually set a desired dose of drug shown in display window 126 and which can then be expelled when the release button 127 is actuated. Depending on the type of expelling mechanism embodied in the drug delivery device, the expelling mechanism may comprise a spring which is strained during dose setting and then released to drive the piston rod when the release button is actuated. Alternatively the expelling mechanism may be fully manual in which case the dose ring member and the release button moves proximally during dose setting corresponding to the set dose size, and then moved distally by the user to expel the set dose. The cartridge is provided with distal coupling means in the form of a needle hub mount 182 having, in the shown example, an external thread 185 adapted to engage an inner thread of a corresponding hub of a needle assembly. In alternative embodiments the thread may be combined with or replaced by other connection means, e.g. a bayonet coupling.

Figure 2:
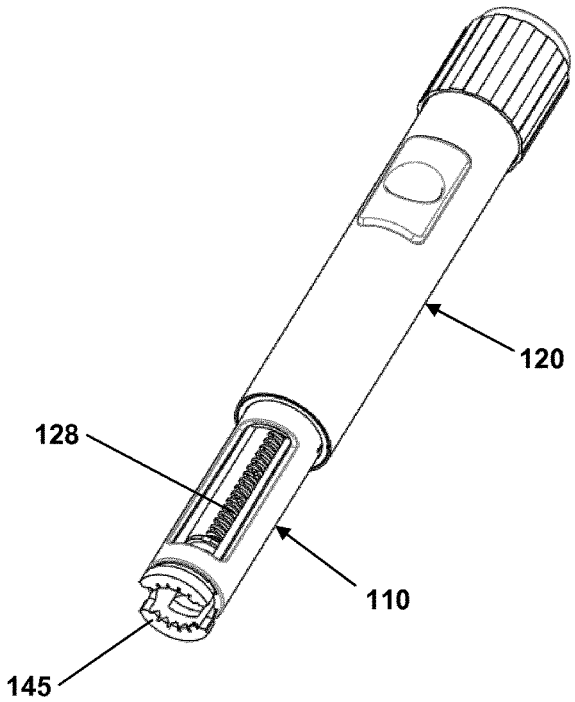

The cartridge holder comprises a distal opening adapted to receive a cartridge. More specifically, the cartridge holder comprises an outer rotatable tube member 170 operated by the user to control movement of gripping means to thereby open and close gripping shoulders 145 configured to grip and hold a cartridge. FIG. 2 shows the device with the cartridge removed and the gripping shoulders in their unlocked "open" position in which a cartridge can be removed and a new inserted.

As appears, FIG. 1 shows a drug delivery device of the front-loaded type in which a cartridge is inserted through a distal opening in the cartridge holder which in non-removable attached to the main part of the device, however, the drug delivery device may alternatively comprise a cartridge holder adapted to be removed from the device main portion and in which a cartridge is received and removed through the proximal opening.

Figure 3:
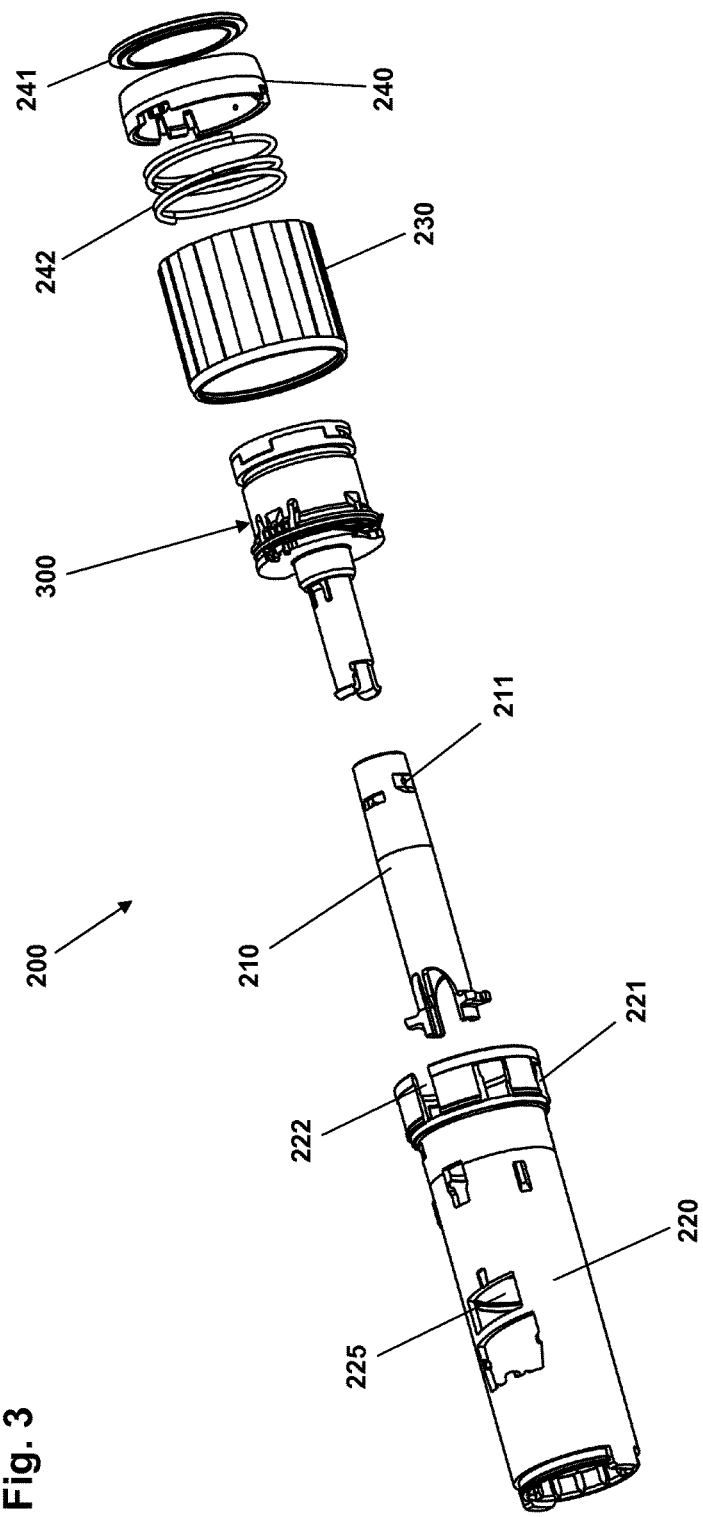
FIG. 3 shows in an exploded view a drug delivery device subassembly comprising a logging module.

With reference to FIG. 3 a subassembly 200 for a drug delivery device will be described, the subassembly comprising a logging module in combination with parts of the drug delivery device being directly functionally related to the incorporation and operation of logging unit. More specifically, the subassembly comprises an electronically controlled logging module 300, an inner tube member 210, a generally cylindrical inner housing member 220, a dial ring member 230 and a button assembly comprising a button ring 240, a button window 241 and a button spring 242. The inner housing member is configured to be arranged inside an outer housing member providing the exterior of the drug delivery device.

Figure 4:
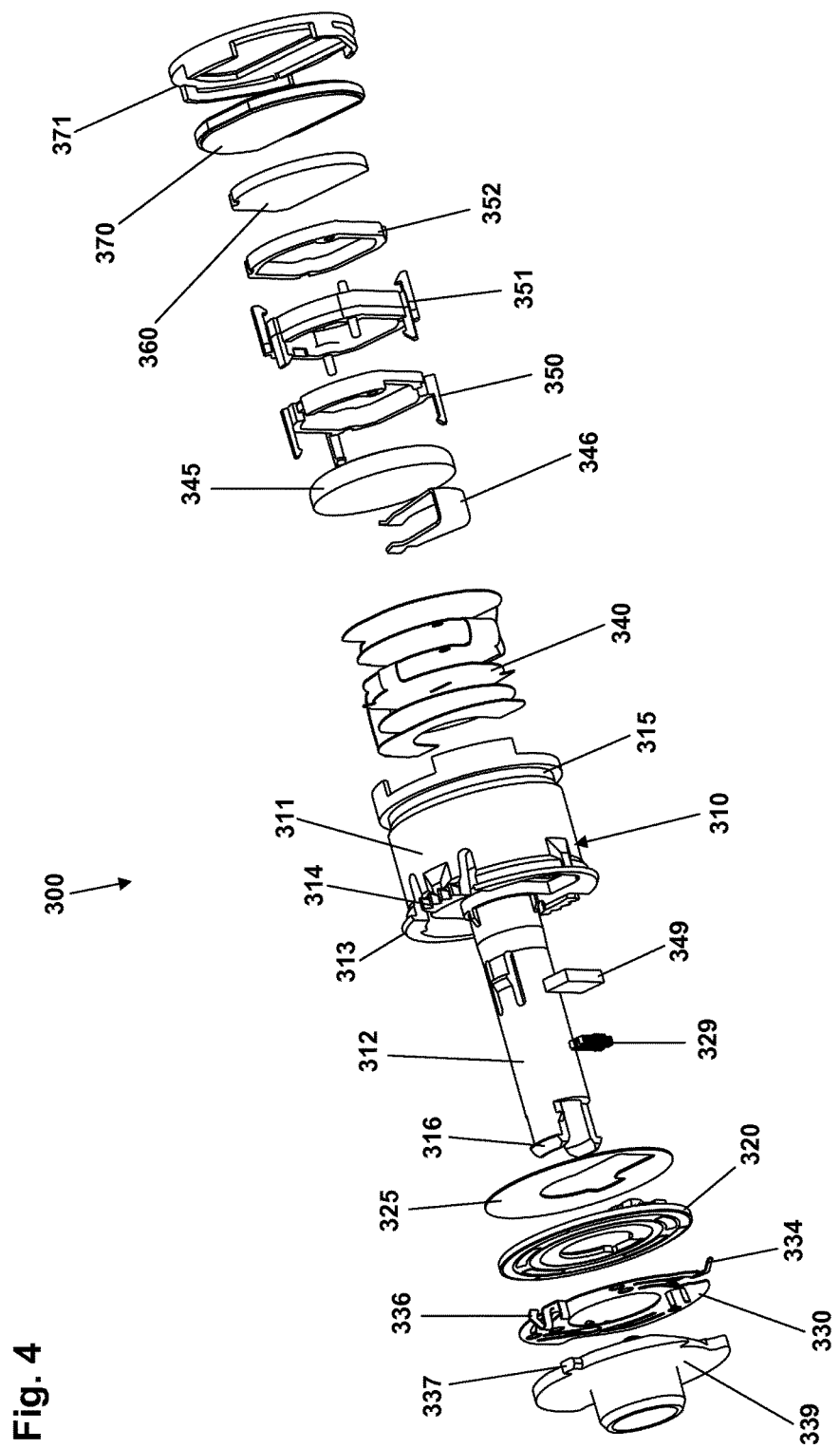
FIG. 4 shows an exploded view of the logging module of FIG. 3, FIGS. 5 and 6 show first respectively second rotary sensor parts of the module of FIG. 3.

The different components of the logging module 300 are shown in FIG. 4. More specifically, the logging module comprises a housing member 310 having a barrel-shaped proximal main portion 311 with a distally extending tube portion 312, a mounting foil member 313, a disc-formed first rotary sensor part 320 onto which a first connector 329 is to be mounted, a disc-formed second rotary sensor part 330, a rotary sensor holder 339 with a lateral projection 337, a flexible PCB 340 folded in a multi-layered stack and onto which a second connector 349 is to be mounted, a battery 345 and battery clip 346, a number of mounting rings 350, 351, 352, an antenna 360, an LCD 370 and an LCD frame 371. Alternatively an OLED or another desirable display technology could be used. On the PCB electronic processor circuitry components are mounted, e.g. micro-controller, display driver, memory and wireless communication means. As will be described below in greater detail the first rotary sensor part 320 comprises a plurality of arc-formed discreet contact areas, and the second rotary sensor part 330 comprises a plurality of flexible contact arms of which one provides an axial switch having a laterally extending projection 334.

Figure 5:
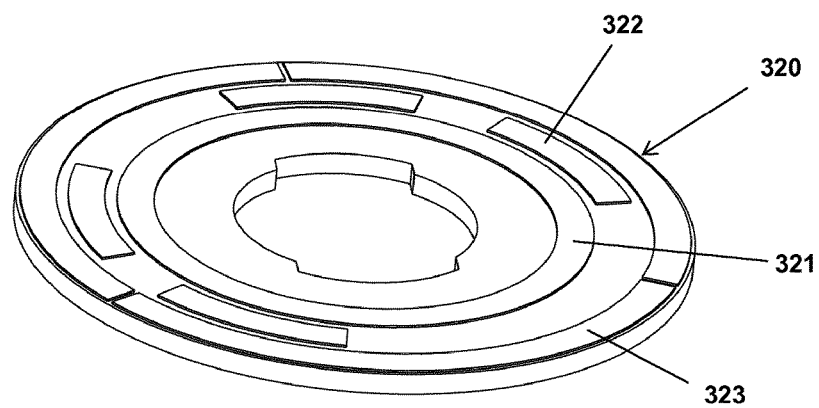

FIG. 5 shows the first rotary sensor part 320 comprising a ring-formed disc formed from circuit board material and on which a number of contact areas (or segments) has been plated on forming three concentric rings, an inner, an intermediate and an outer ring. In the shown embodiment the inner ring is a single contact segments 321 used as ground (i.e. reference), the intermediate ring comprises four discrete arch-formed position contact segments 322 arranged with a certain circumferential distance there between, and the outer ring comprises three discrete arch-formed switch contact segments 323 arranged with only a small circumferential gap there between, the segments being individually connected to a given contact terminal of the multi-terminal connector 329 mounted on the rear (proximal) face of the disc. If a given segment is not connected to a terminal it can be considered a passive segment.

Figure 6:
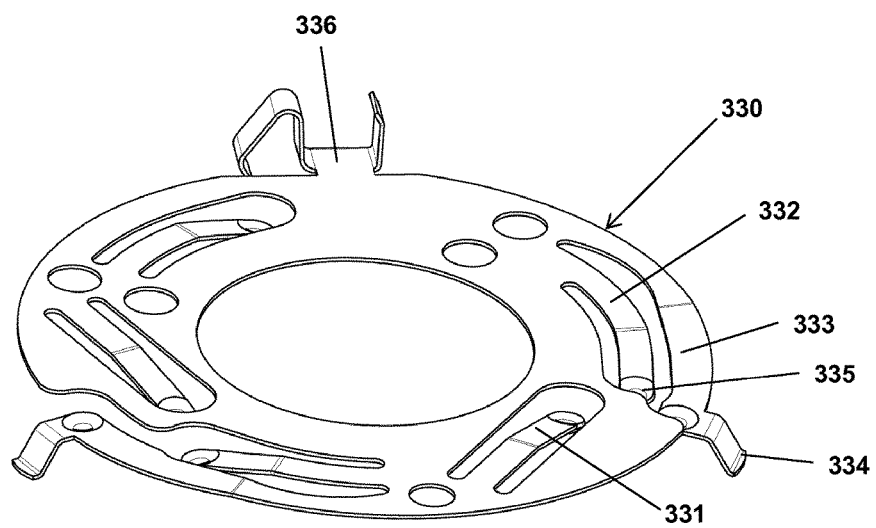

The second rotary sensor part 330 shown in FIG. 6 is in the form of a metallic disc comprising a number of flexible arc-formed contact arms protruding proximally, the distal end of each contact arm comprising a dome-formed contact point 335 (facing downwards in the figure) adapted to create a galvanic connection with a given contact segment. The contact arms are arranged corresponding to the three concentric rings of the first rotary sensor part. More specifically, the second rotary sensor part comprises two inner contact arms 331, three intermediate contact arms 332 and two outer contact arms 333.

In this way a given pair of contact arms provides a combined contact structure adapted to create electric contact between two contact segments. In the shown embodiment the two inner ground contact arms 331 are provided to be in contact with the single ground contact segment 321 of the inner concentric ring, the three position contact arms 332 are provided to create contact with the four position contact segments 322 of the intermediate concentric ring, and the two outer switch contact arms 333 are provided to be in contact with the three switch contact segments 323 of the outer concentric ring, the outer switch contact arms carrying a laterally extending projection 334. Indeed, for the intermediate and outer contact arms the rotational position between the two sensor parts will determine which contact segment is engaged with a given contact arm. The two outer switch contact arms 333 are in the shown embodiment used to provide redundancy for the axial switch, however, in cooperation with the switch contact segments of the outer ring they could additionally be used to provide rotational information.

The second rotary sensor part further comprises a gripping part 336 adapted to engage the projection 337 on the rotary sensor holder 339 to prevent rotational movement there between.

In the shown embodiment the intermediate arms and contact segments provide the rotary sensor contacts whereas the outer arms and contact segments provide an axial switch as will be described in greater detail below.

The four position contact segments 322 represent in combination with the ground segment four position contacts having an "off" state when not connected by the ground contact arms 331 and any of the position contact arms, and an "on" state when connected by the ground contact arms and a given position contact arm.

For a given rotational position the electrically connected arms create a number of "on" galvanic contacts between given pairs of contact segments, other non-connected areas representing an "off" contact condition. The shown rotary sensor has a resolution of 15 degrees, i.e. 24 steps for a full rotation, such that for each 15 degrees of rotation a predetermined change in which of the individual position rotary contacts are on and off is created. As each of the shown contact segments is connected to the electronic processor circuitry 340 it is possible to determine the relative rotational position between the two rotary sensor parts.

Figure 7:
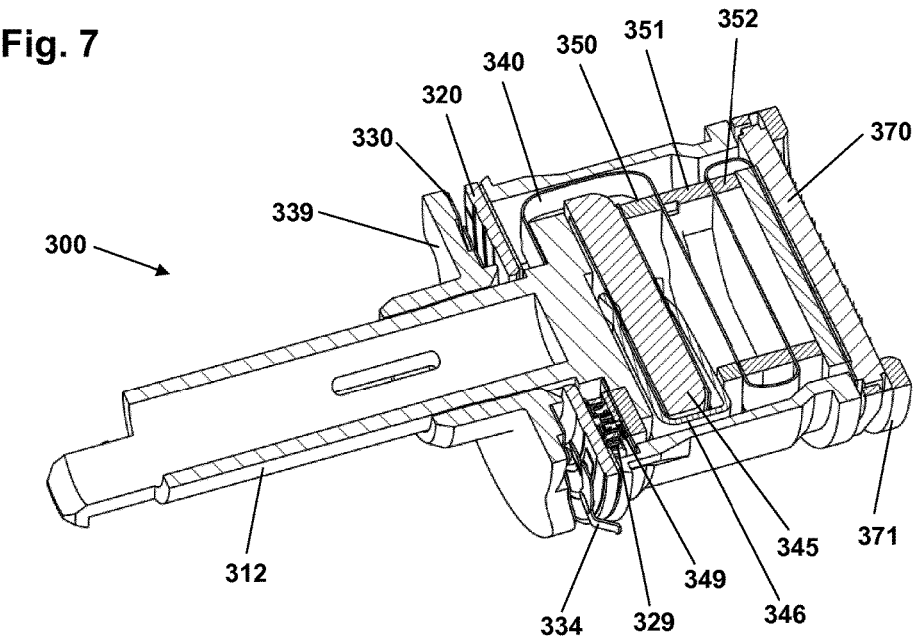
FIG. 7 shows the logging module of FIG. 4 in an assembled state.

FIG. 7 shows the logging module 300 in an assembled state. The flexible PCB 340 with its mounted components and the antenna have been mounted in a sandwich configuration with the mounting rings 350, 351, 352 providing the required spacing and attachment via e.g. gluing or adhesives, the battery 345 being attached to the PCB via battery clip 346. The PCB sandwich is mounted with a "tongue" threaded through a distal opening in the housing 311 button portion and held in place with adhesive mounting foil member 325 (see FIG. 4) during assembly. The first rotary sensor part 320 is mounted non-rotationally on the tube portion 312 and connected to the PCB via the connectors 329, 349. The second rotary sensor part 330 is mounted non-rotationally and axially fixed on the rotary sensor holder 339 which is mounted rotationally free but axially fixed on the tube portion 312. By this arrangement the flexible rotary sensor arms are held in sliding contact with the contact surfaces. The LCD 370 is mounted on top of the PCB sandwich which together is held in place in the housing barrel by the display frame 371 which is permanently attached to the housing by e.g. welding. As appears, in this way an electronic logging module is provided comprising a distally arranged rotatable sensor part. As shown in FIG. 4 the housing main portion 311 comprises a circumferential distal flange 313 with a number of proximally projecting teeth 314 and a circumferential proximal groove 315. The tube portion 312 is provided with distal snap connectors 316 adapted to engage corresponding openings 211 in the inner tube member 210.

Figure 8:
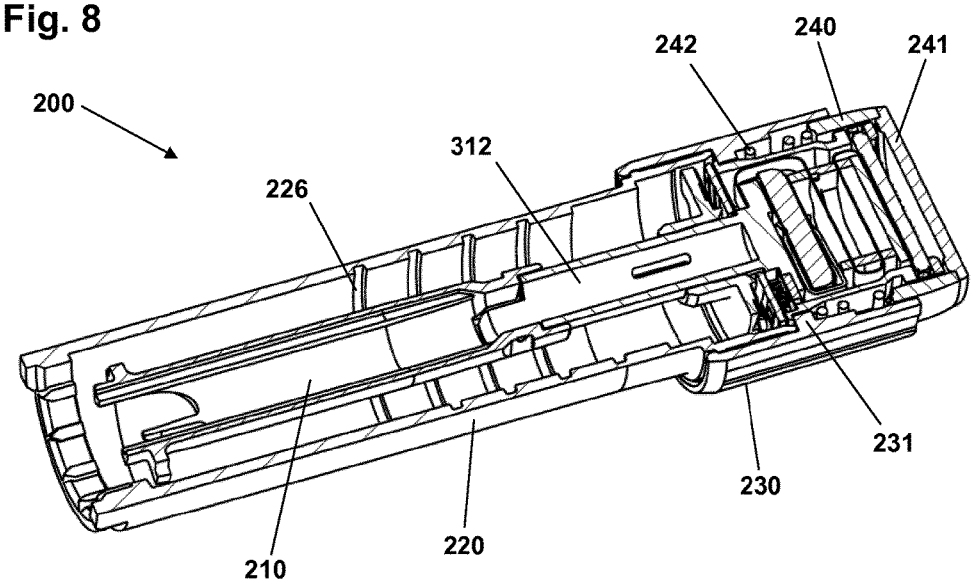
FIG. 8 shows a cross-sectional view of the subassembly of FIG. 3 in an assembled state.

FIG. 8 shows a cross-sectional view of the subassembly 200 in an assembled state. The term "subassembly" does not imply that the shown parts necessary are assembled to provide a subassembly as shown and which can be used in an assembly process for a given drug delivery device. In contrast, the shown logging module of FIG. 7 may be provided in the shown form as a "real" subassembly. Referring to the parts shown in FIGS. 3 and 4, the inner tube member 210 is connected rotationally and axially locked to the distal tube portion 312 of the logging module. This arrangement is mainly for the purpose of moulding and subsequent assembly. The dial ring member 230 is mounted on the proximal portion of the housing member 220 on which it is allowed to freely rotate but not move axially. The dial ring member 230 comprises an inner circumferential coupling flange 231 with a plurality of distally facing teeth adapted to engage the proximally facing teeth 314 of the logging module to thereby rotationally lock the two components during engagement. The housing member 220 comprises first and second openings or cut-outs 221, 222 (see FIG. 3) adapted to engage respectively the rotary sensor holder lateral projection 337 and the axial switch lateral projection 334, this ensuring non-rotational engagement between the second rotary sensor part and the housing yet allows axial movement.

The button 240 with the window 241 attached is mounted on the module housing in gripping engagement with the circumferential groove 315, this allowing the button to rotate relative to the module housing. The axially compressed button assembly spring 242 is arranged in the circumferential gap between the module housing and the dial ring member and held in place between a distally facing ring portion of the button ring and the proximally facing portion of the coupling flange. In this way the spring provides an axial force biasing the module proximally into non-rotational engagement with the dial ring member 230 via the coupling flange, however, when a distally directed force is applied to the module via the button the module can be moved distally and thereby out of the rotational coupling with the dial ring member, this allowing the logging module main housing to rotate relative to the dial ring member.

Figure 9A:
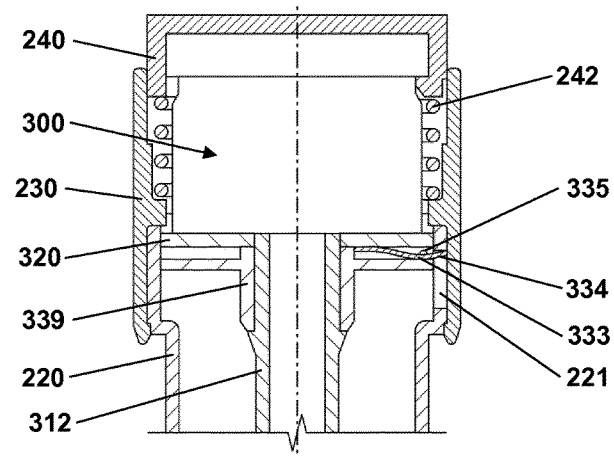
FIGS. 9A-9C show operation of an axial switch of the logging module in different operational states.
Figure 9B:
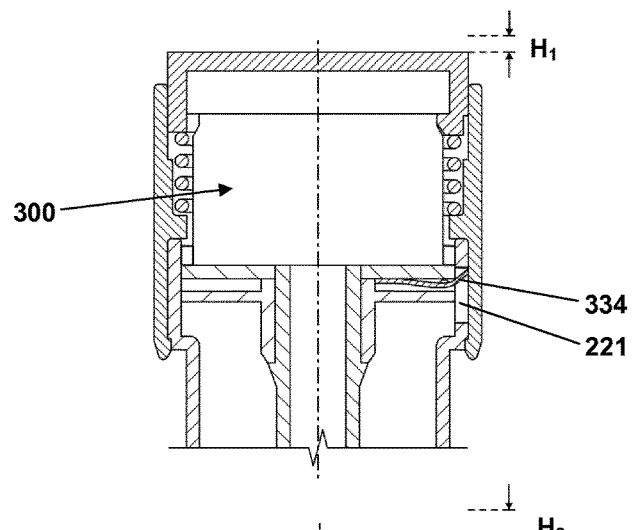
Figure 9C:
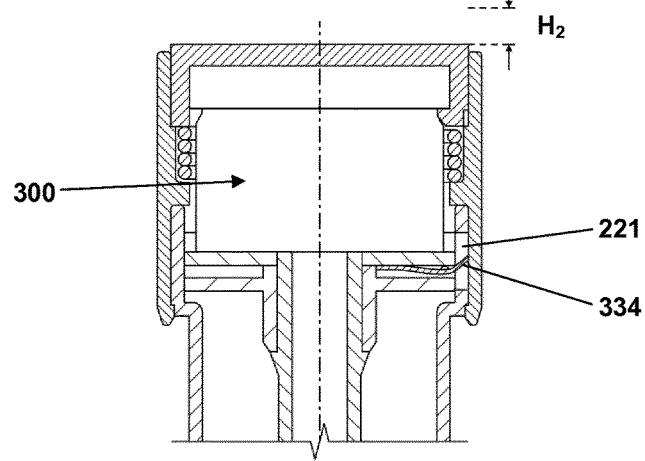

As indicated above, the shown rotary sensor comprises an axial switch, this switch serving to detect an axial position of the logging module relative to (here) the housing member 220. More specifically, FIG. 9A shows the logging module 300 biased into an initial proximal position by the button spring 242, FIG. 9B shows the logging module in an intermediate position in which it has been moved distally by the distance $H_1$, and FIG. 9C shows the logging module in an actuated distal position in which it has been moved distally by the distance $H_2$. In all three states the axial switch lateral projection 334 is positioned in the corresponding housing opening 221 and rotationally locked to the housing via the rotary sensor holder 339. As appears, in FIG. 9A the switch projection 334 engages a proximal edge of the opening and the flexible switch arm 333 with the contact point 335 is thereby held out of contact with the first rotary sensor part 320, in FIG. 9B the switch projection 334 still engages the proximal edge of the opening, however, the logging module has been moved distally and thereby the first rotary sensor part 320 has been moved into contact with the switch arm 333, this bringing the axial switch into an "on" state detectable by the logging module circuitry, and in FIG. 9C the logging module has been moved further distally to its actuated distal position. The switch projection 334 has been moved out of engagement with the proximal edge of the opening, the axial switch thus remaining in its "on" state. In an exemplary embodiment the axial movement between the different positions may be e.g. 1.5 mm, this ensuring that the expelling mode is safely registered by the axial switch before the dosing mechanism is actually released. The axial switch could also be used to control the functioning of the logging module when no dose has been set, see below.

The parts of the subassembly 200, apart from module 300, as shown in FIG. 3 represent "generic" parts of a drug expelling mechanism having properties which are relevant for the implementation of embodiments of the present invention. More specifically, the shown module 300 is adapted to be implemented in a drug delivery device having a housing, dose setting means allowing a user to set a dose of drug to be expelled, and a rotational member adapted to rotate corresponding to a set and/or expelled dose. In the shown subassembly the inner tube member 210 represents a "generic" rotational member.

Although not part of the present invention, in the following a short description of a drug expelling mechanism into which the shown inner tube member 210 could be integrated will be described. When setting a dose to be expelled the user rotates the dial ring member 230 and thereby the inner tube member 210 to a given rotational position representing a desired dose, this straining a torsional spring member arranged around the tube member and attached at its proximal end to a housing proximal portion and at its distal end to the tube member distal portion. A ratchet coupling arranged at the distal end of the inner tube member serves to hold the now rotationally biased tube member in the set position. A scale drum is coupled to and rotates with the tube member, the scale drum having a threaded connection with the housing (e.g. threads 226 in FIG. 3) whereby a spirally arranged series of numeric values is moved relative to a window in the housing (e.g. opening 225 in FIG. 3), the shown number indicating the presently set dose. To release the set and loaded mechanism the user pushes a proximal release button whereby the inner tube member is moved distally. By this action the ratchet coupling (serving as a release member) is released and the inner tube member is moved into engagement, directly or indirectly, with a rotational drive member, the drive member being arranged to rotate a piston rod which due to a threaded engagement with the housing is moved distally to thereby set the dose. As the tube member rotates backwards, thereby driving the piston rod distally, also the scale drum is rotated backwards and reaches its initial "zero" position together with the tube member. This kind of mechanism is known from e.g. the FlexTouch® drug delivery pen device marketed by Novo Nordisk for the injection of e.g. insulin formulations.

As appears, in the described exemplary mechanism the inner tube member 210 (to which the main portion of the logging module 300 is rigidly mounted) rotates relative to the housing 220 during both setting and expelling of a given dose. As the second rotary sensor part 330 is rotationally locked to the housing, also the two rotary sensor parts 320, 330 rotate relative to each other during both setting and expelling of a given dose. As this is merely an exemplary mechanism, other mechanisms can be envisaged in which a given member rotates only during setting or expelling.

This said, in the shown embodiment the logging module is adapted to detect rotation in both directions corresponding to a set dose and an expelled dose. In the shown embodiment the logging module is further provided with an axial switch allowing the module to detect whether the mechanism is in the setting or expelling mode, however, this is an optional feature. In the shown embodiment the code pattern has a step "resolution" of 15 degrees of rotations which for a given drug formulation and delivery device combination may correspond to 1 unit (IU) of insulin. Indeed, for a drug formulation having the double concentration a 7.5 degree rotary resolution would be necessary to register dose steps corresponding to 1 IU of insulin. The rotary sensor comprising the rotary contacts and the associated electronic processor circuitry could be designed to detect the amount of rotation using a number of designs, e.g. each 15 degrees increment may be counted, or a given position may be detected absolutely within sectors of e.g. 120 or 360 degrees, a counter registering the number of completed sectors. Such a counter could be implemented using the switch arms and outer contact areas described with reference to FIGS. 5 and 6. With a "counting" design it is important that the first increment is registered, however, modern electronics can be operated in a low-power "on" state avoiding the delay normally associated with a wake-up change of state from a "sleep" state to an "on" state.

In an exemplary embodiment the rotary sensor is designed to count the number of steps during setting and to count down the number of steps during expelling, with the expelling steps being registered in the log as the dose being expelled. By counting in both directions proper registering and functioning of the logging module can be assured to a high degree. As a given dose of drug, especially if large, may be divided and injected with a given pause, the logging module may be programmed to log two dose amounts expelled within a given time window, e.g. 15 minutes, as one dose.

The logging module may be configured to store and show data in different ways. To many users the time since last dose and the size of that dose are the most important values. To other users and/or a medical practitioner an overview of the entire log for a given period, e.g. a week or a month, may be of importance. To allow such an overview the logging module may be provided with output means allowing the dose log to be transferred, e.g. by NFC transfer, to an external display device, e.g. a smartphone or computer for better graphic overview, see below.

To ensure that the full dose is expelled the logging module may be set up to display the last expelled dose only when the expelling mechanism has been returned to zero. Otherwise a given "half" dose will be stored in the log but not displayed. For example, if a dose of 40 IU is dialled and 20 IU are expelled immediately thereafter the display will not show data for that delivery. To have the dose shown in the display the user may expel the remaining dose and the combined dose of 40 IU together with a time stamp will be shown in the display. Alternatively the user may dial the expelling mechanism back to zero and the display will show 20 IU, or the user may dial the expelling mechanism back to 10 IU and expel the 10 IU and the display will show 30 IU. Indeed, for the expelled amounts to be combined the two (or more) doses will have to be expelled within the above-described time window, e.g. 15 minutes. Otherwise only the last portion of the dose will display, the first portion being stored merely as an entry in the log.

Figure 10:
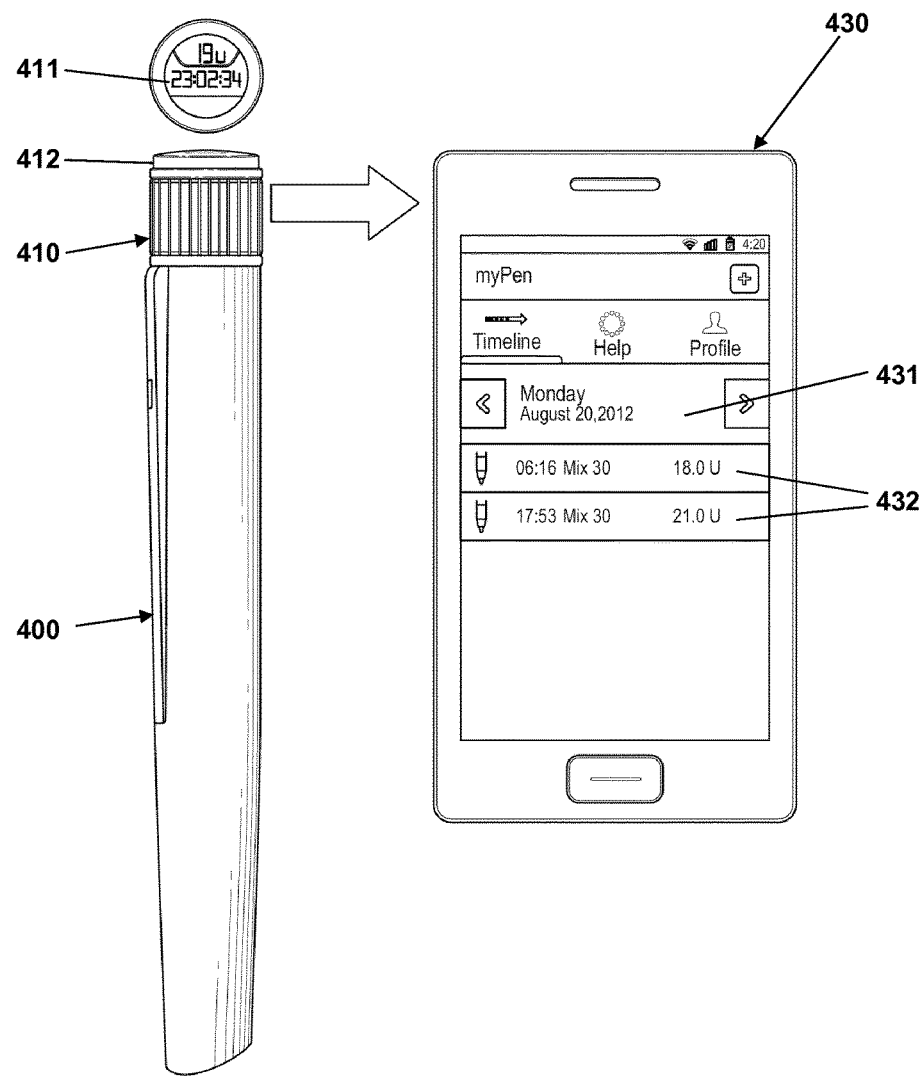
FIG. 10 shows a drug delivery pen provided with a logging module and in communication with a smartphone.

The display can be configured to show data in different formats. For example, the display 411 of FIG. 10 is a two-line display in which time is shown using a HH:MM:SS stop watch design, this providing that the time since the last dose expelled from the device can be shown with a running second counter allowing a user to easily identify the shown information as a counting time value. After 24 hours the display may continue to display time in the HH:MM:SS format or change to a day and hour format.

To save energy the display will turn off after a predetermined amount of time, e.g. 30 seconds. To turn on the display again the user may e.g. press the button thereby using the axial switch to turn on the display, or the display may be turned on when the dose dial is turned away from and then back to zero.

A user may desire to check the dose log directly on the module display. Toggling through the dose log could also be controlled by the axial switch, e.g. two fast pushes on the button 412 will bring the module into log display mode, each consecutive push on the button recalling the next log entry. The module may leave the log display mode automatically after a given amount of time, or the user may bring the module into normal display mode by e.g. dialling back and forth as described above. As an alternative, the electronic module may be provided with other types of input means, e.g. a motion sensor which would allow a user to turn on the display by shaking or tapping, or a touch sensor integrated in the display as is well known from e.g. smartphones which would allow a user to turn on the display by swiping a finger across the display.

FIG. 10 shows a drug delivery pen 400 provided with a logging module 410 as described above and arranged next to a smartphone 430 configured to receive logging data from the logging module via wireless communication, e.g. NFC. As appears, the logging module is provided with a display configured to indicate the size of the last dose and the time since the last dose using the stopwatch display mode.

In order to communicate with the logging module the smartphone has been provided with specific "insulin diary" software. When the software is activated to initiate data transfer the smartphone NFC transmitter will transmit specific code which will wake up any nearby logging module which will then retransmit a unique code identifying the specific module. If a specific code is received for the first time the user is asked to confirm pairing and is asked to select from a list the given drug that should be associated with the given logging module, e.g. "Mix 30" as shown. In this way the smartphone can create an insulin diary covering more than one drug. In the described simple "manual" set-up the user has to ensure that a correct cartridge, e.g. with Mix 30 insulin, is loaded in a drug delivery pen which has been associated with that type of drug. Indeed, other set-ups can be envisaged, e.g. a given pen may be (mechanically) coded to only accept a given type of cartridge with the designated type of drug, or the pen and logging module may be provided with the ability to identify different types of cartridges and thus types of drug.

In the shown embodiment log data from a logging module associated with a Mix 30 insulin has been transferred. In the exemplary user interface the user can toggle back and forth between different day views, each day view showing the different amounts of drug delivered together with a real time value. In FIG. 10 on a given day 431 first and second amounts 432 of Mix 30 has been delivered with the time and amount shown for each delivery.

Figure 11:
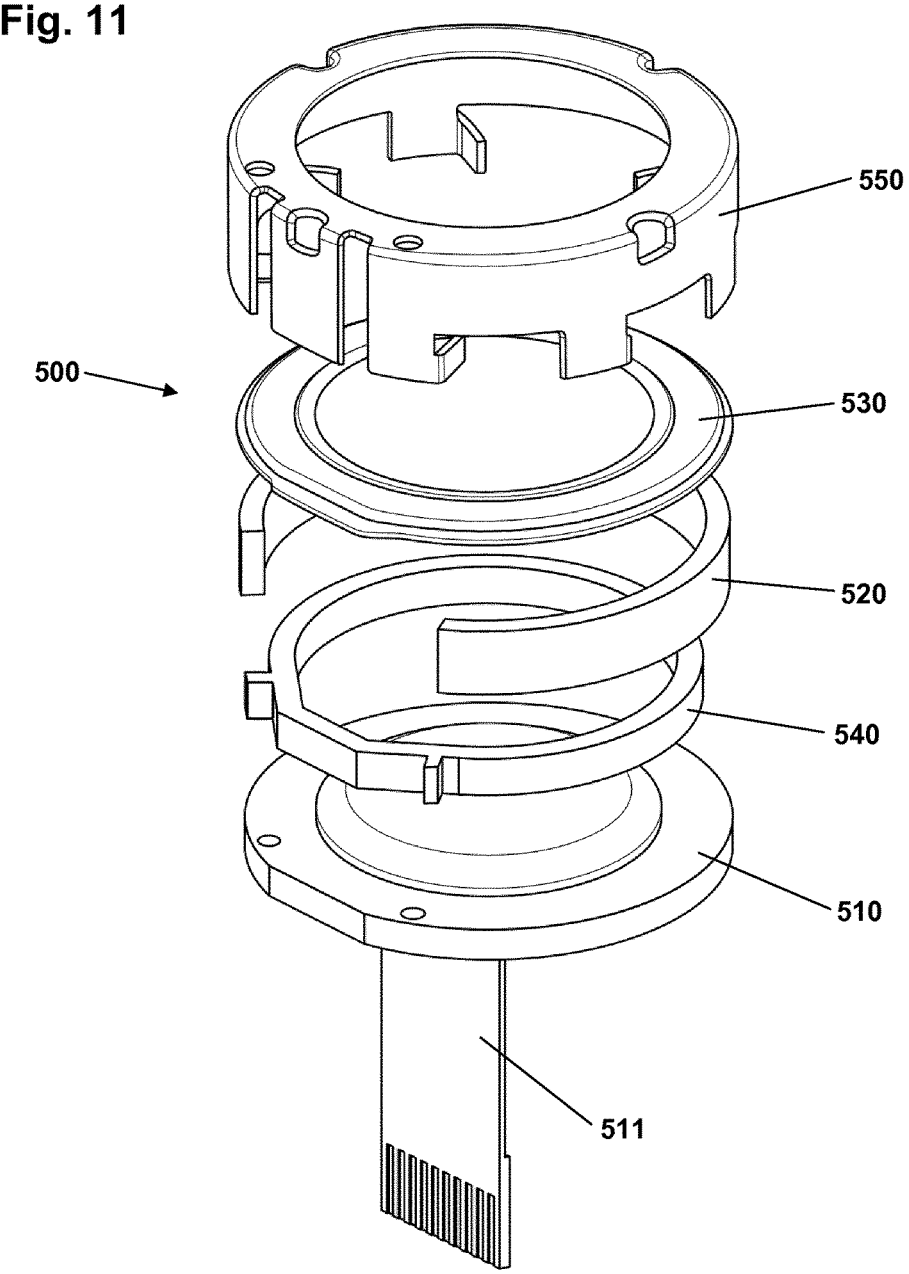
FIG. 11 shows in an exploded view a display assembly.

In the embodiment of FIG. 7 the LCD has been attached to the PCB using traditional ACF (Anisotropic Conductive Film) bonding, however, in FIG. 11 an alternative solution for attaching the LCD to a PCB is shown. More specifically, FIG. 11 shows in an exploded view a display assembly 500 comprising a PCB 510 with a flexible connector 511, a curved elastomeric connector 520 (e.g. a Zebra® connector), a segmented LCD (e.g. numeric or dot-matrix) 530, a mounting ring 540 and a housing ring 550. The LCD comprises a connector array with a plurality of connectors arranged in a first curved configuration a long at a part of the curved circumferential portion, e.g. 300 degrees, and the PCB comprises a corresponding connector array having a plurality of connectors arranged in a second curved configuration corresponding at least in part to the first curved configuration. The curved elastomeric connector is adapted to establish a plurality of electrical connections between the connectors of the two connector arrays when the LCD, the PCB and the elastomeric connector is arranged in conducting contact. In an assembled state the housing ring is attached to the PCB thereby holding the remaining components into forced engagement with each other.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A drug delivery device comprising:
   a housing,
   a drug-filled cartridge or structure for receiving a drug-filled cartridge, the cartridge comprising an axially displaceable piston and a distal outlet portion,
   drug expelling structure comprising:
      dose setting structure allowing a user to set a dose of drug to be expelled,
      an axially displaceable piston rod adapted to move the piston of a cartridge in a distal direction to thereby expel drug from the cartridge, and
      a rotational member adapted to rotate relative to the housing and corresponding to a set and/or expelled dose,
   sensor structure adapted to detect a set and/or an expelled dose, comprising:
   a first portion mounted to and rotating with the rotational member, comprising:
      electronic processor circuitry, and
      a first rotary sensor part,
   a second portion comprising
      a second rotary sensor part mounted non-rotationally relative to the housing,
   whereby the first and second rotary sensor parts rotate relative to each other during setting and/or expelling of a dose of drug.

2. A drug delivery device as in claim 1, wherein:
the rotational member is rotated from an initial position to a set position when a dose is set, and
the rotational member is rotated from the set position to the initial position when the set dose is expelled.

3. A drug delivery device as in claim 1, wherein the rotational member is adapted to move axially between an initial and an actuated position, the first portion being mounted to move axially with the rotational member.

4. A drug delivery device as in claim 3, wherein the second portion is mounted to move axially with the rotational member.

5. A drug delivery device as in claim 3, wherein the sensor structure is adapted to detect when the rotational member is moved axially between the initial and the actuated position.

6. A drug delivery device as in claim 1, wherein the electronic processor circuitry comprises logging structure adapted to create a log for dose amounts of drug expelled from a cartridge by the drug expelling structure, wherein the dose amounts are calculated based on relative rotation between the first and second rotary sensor parts during setting and/or expelling of a dose of drug.

7. A drug delivery device as in claim 1, wherein the first portion comprises a display.

8. A drug delivery device as in claim 7, wherein the display is turned off during rotation of the first portion.

9. A drug delivery device as in claim 1, wherein the electronic processor circuitry comprises transmitter structure adapted to transmit stored data to an external receiver.

10. A drug delivery device as in claim 1, wherein the sensor structure is provided in the form of an electronic assembly comprising the first and the second portion, the first portion being in the form of an electronic module, the second portion being rotationally mounted on the electronic module,
wherein the electronic module and the rotational member comprises corresponding interconnecting structure allowing the electronic module to be mounted rotationally locked to the rotational member, and
wherein the second portion and the housing comprises corresponding interconnecting structure allowing the second rotary sensor part to be mounted rotationally locked relative to the housing.

11. A drug delivery device as in claim 1, wherein:
the first rotary sensor part comprises a pattern of a plurality of individual electrically conducting sensor areas connected to the electronic processor circuitry, and
the second rotary sensor part comprises at least one contact structure adapted to engage and connect different sensor areas as the first and second part of the rotary sensor rotate relative to each, the connections being indicative of a rotational position between the first and second portions.

12. A drug delivery device as in claim 11, wherein:
one of the contact structures comprises an axial switch contact having a connected position in which the switch contact is in contact with a sensor area and a dis-connected position in which the switch contact is not in contact with a sensor area, and
the axial switch contact is adapted to be moved between the connected position and the dis-connected position when the second rotary sensor part is moved axially relative to the housing.

13. A drug delivery device as in claim 12, wherein the second rotary sensor part is in the form of a metallic disc member comprising a plurality of integrally formed flexible arms forming the contact structures, at least one of the flexible arms being axially moveable to form a flexible switch arm comprising the axial switch contact.

14. A drug delivery system comprising:
a drug delivery assembly comprising:
a housing,
a drug-filled cartridge or structure for receiving a drug-filled cartridge, the cartridge comprising an axially displaceable piston and a distal outlet portion,
drug expelling structure comprising:
dose setting structure allowing a user to set a dose of drug to be expelled,
an axially displaceable piston rod adapted to move the piston of a cartridge in a distal direction to thereby expel drug from the cartridge,
a rotational member adapted to rotate corresponding to a set and/or expelled dose, and
an axially moveable release member adapted to release the drug expelling structure to thereby expel the set dose of drug,
first and second modules each comprising:
first coupling structure allowing the module to be mounted non-rotationally to the rotational member,
wherein a mounted module serves to transfer an axially directed force acting to move the release member,
wherein the first module comprises no electronic processor circuitry, and
wherein the second module is a self-contained sensor module, comprising:
a first portion comprising:
the first coupling structure,
electronic processor circuitry, and
a first rotary sensor part,
a second portion comprising:
a second rotary sensor part mounted rotationally relative to the housing, and
second coupling structure allowing the second rotary sensor part to be mounted non-rotationally to the housing,
whereby the first and second rotary sensor parts of a mounted sensor module rotate relative to each other during setting and/or expelling of a dose of drug to thereby detect a set and/or expelled dose.

15. A drug delivery system as in claim 14, further comprising a rotatable dose setting member, the rotational member being adapted to rotate corresponding to a set dose,
wherein a mounted module serves to transfer a rotational movement of the dose setting member to the rotatable member.

* * * * *